(12) United States Patent
Mickus et al.

(10) Patent No.: US 12,251,130 B2
(45) Date of Patent: Mar. 18, 2025

(54) SURGICAL ACCESS DEVICE HAVING A BALLOON AND METHODS FOR MANUFACTURING THE SAME

(71) Applicant: Covidien LP, Mansfield, MA (US)

(72) Inventors: Jason Mickus, Avon, CT (US); Kevin M. Desjardin, Prospect, CT (US); Christopher A. Tokarz, Wallingford, CT (US); Astley C. Lobo, West Haven, CT (US)

(73) Assignee: Covidien LP, Mansfield, MA (US)

( * ) Notice: Subject to any disclaimer, the term of this patent is extended or adjusted under 35 U.S.C. 154(b) by 264 days.

(21) Appl. No.: 17/246,781

(22) Filed: May 3, 2021

(65) Prior Publication Data

US 2022/0346832 A1    Nov. 3, 2022

(51) Int. Cl.
*A61B 17/34* (2006.01)
*A61M 25/10* (2013.01)

(52) U.S. Cl.
CPC ..... *A61B 17/3423* (2013.01); *A61M 25/1002* (2013.01); *A61M 25/1029* (2013.01); *A61B 2017/3486* (2013.01); *A61M 2025/1031* (2013.01); *A61M 2025/1086* (2013.01)

(58) Field of Classification Search
CPC ............ A61B 17/3421; A61B 17/3423; A61B 2017/3419; A61B 2017/3441; A61B 2017/3482; A61B 2017/3484; A61B 2017/3486; A61M 25/04; A61M 2025/1002; A61M 2025/1031; A61M 2025/1086; A61J 15/0042; A61J 15/0049
See application file for complete search history.

(56) References Cited

U.S. PATENT DOCUMENTS

| | | | |
|---|---|---|---|
| 397,060 | A | 1/1889 | Knapp |
| 512,456 | A | 1/1894 | Sadikova |
| 1,213,005 | A | 1/1917 | Pillsbury |
| 1,780,912 | A | 11/1930 | Gau |
| 1,810,466 | A | 6/1931 | Deutsch |
| 2,313,164 | A | 3/1943 | Nelson |

(Continued)

FOREIGN PATENT DOCUMENTS

| | | |
|---|---|---|
| DE | 10001695 A1 | 2/2001 |
| DE | 102009014527 A1 | 9/2010 |

(Continued)

OTHER PUBLICATIONS

International Search Report and Written Opinion issued in corresponding International Application No. PCT/IB2022/053817 mailed Aug. 19, 2022, 19 pages.

*Primary Examiner* — Diane D Yabut
(74) *Attorney, Agent, or Firm* — Draft Masters IP, LLC

(57) ABSTRACT

A method of forming a balloon for a surgical access device includes positioning a molding material into a channel defined in a first mold half of a mold and mounting a second mold half onto the first mold half to cover the channel and form a cavity within the mold. The first and second mold halves each includes vent holes extending therethrough that are in fluid communication with the cavity. The method also includes expanding the molding material to conform to the shape of the cavity to form a balloon including protrusions extending radially outwardly therefrom. The protrusions are formed by engagement of the molding material with the vent holes.

10 Claims, 6 Drawing Sheets

(56) References Cited

U.S. PATENT DOCUMENTS

| | | |
|---|---|---|
| 2,541,516 A | 2/1951 | Ivory et al. |
| 2,812,758 A | 11/1957 | Blumenschein |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,782,370 A | 1/1974 | McDonald |
| 3,800,788 A | 4/1974 | White |
| 3,807,393 A | 4/1974 | McDonald |
| 3,882,852 A | 5/1975 | Sinnreich |
| 3,896,816 A | 7/1975 | Mattler |
| 3,961,632 A | 6/1976 | Moossun |
| 3,965,890 A | 6/1976 | Gauthier |
| RE29,207 E | 5/1977 | Bolduc et al. |
| 4,083,369 A | 4/1978 | Sinnreich |
| 4,130,113 A | 12/1978 | Graham |
| 4,217,889 A | 8/1980 | Radovan et al. |
| 4,243,050 A | 1/1981 | Littleford |
| 4,263,899 A | 4/1981 | Burgin |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,553,537 A | 11/1985 | Rosenberg |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,927,412 A * | 5/1990 | Menasche ......... A61M 25/1002 604/103.08 |
| 4,931,042 A | 6/1990 | Holmes et al. |
| 4,955,895 A | 9/1990 | Sugiyama et al. |
| 5,002,557 A | 3/1991 | Hasson |
| 5,007,900 A | 4/1991 | Picha et al. |
| 5,009,643 A | 4/1991 | Reich et al. |
| 5,030,206 A | 7/1991 | Lander |
| 5,030,227 A | 7/1991 | Rosenbluth et al. |
| 5,052,374 A | 10/1991 | Alvarez-Jacinto |
| 5,074,871 A | 12/1991 | Groshong |
| 5,080,088 A | 1/1992 | LeVahn |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,125,396 A | 6/1992 | Ray |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,169,387 A | 12/1992 | Kronner |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,231,974 A | 8/1993 | Giglio et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,269,754 A | 12/1993 | Rydell |
| 5,279,575 A | 1/1994 | Sugarbaker |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,330,501 A | 7/1994 | Tovey et al. |
| 5,342,307 A | 8/1994 | Euteneuer et al. |
| 5,346,484 A | 9/1994 | Van Lindert |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,391,156 A | 2/1995 | Hildwein et al. |
| 5,397,311 A | 3/1995 | Walker et al. |
| 5,402,772 A | 4/1995 | Moll et al. |
| 5,407,433 A | 4/1995 | Loomas |
| 5,423,745 A * | 6/1995 | Todd ................. A61M 25/1034 604/509 |
| 5,431,173 A | 7/1995 | Chin et al. |
| 5,437,683 A | 8/1995 | Neumann et al. |
| 5,445,615 A | 8/1995 | Yoon |
| 5,460,170 A | 10/1995 | Hammerslag |
| 5,468,248 A | 11/1995 | Chin et al. |
| 5,480,410 A | 1/1996 | Cuschieri et al. |
| 5,490,843 A | 2/1996 | Hildwein et al. |
| 5,503,617 A | 4/1996 | Jako |
| 5,514,091 A | 5/1996 | Yoon |
| 5,514,153 A | 5/1996 | Bonutti |
| 5,520,610 A | 5/1996 | Giglio et al. |
| 5,524,644 A | 6/1996 | Crook |
| 5,540,658 A | 7/1996 | Evans et al. |
| 5,540,711 A | 7/1996 | Kieturakis et al. |
| 5,556,385 A | 9/1996 | Andersen |
| 5,562,677 A | 10/1996 | Hildwein et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,653,705 A | 8/1997 | de la Torre et al. |
| 5,656,013 A | 8/1997 | Yoon |
| 5,667,479 A | 9/1997 | Kieturakis |
| 5,667,520 A | 9/1997 | Bonutti |
| 5,697,891 A | 12/1997 | Hori |

(56) References Cited

U.S. PATENT DOCUMENTS

| | | |
|---|---|---|
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,103 A | 3/1998 | Picha et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,660 A | 5/1998 | Tyagi |
| 5,755,661 A | 5/1998 | Schwartzman |
| 5,755,693 A | 5/1998 | Walker et al. |
| 5,762,604 A | 6/1998 | Kieturakis |
| 5,772,583 A | 6/1998 | Wright et al. |
| 5,772,680 A | 6/1998 | Kieturakis et al. |
| 5,776,110 A | 7/1998 | Guy et al. |
| 5,779,629 A | 7/1998 | Hohlen |
| 5,779,728 A | 7/1998 | Lunsford et al. |
| 5,788,630 A | 8/1998 | Furnish |
| 5,797,947 A | 8/1998 | Mollenauer |
| 5,803,901 A | 9/1998 | Chin et al. |
| 5,803,921 A | 9/1998 | Bonadio |
| 5,810,721 A | 9/1998 | Mueller et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,846,193 A | 12/1998 | Wright |
| 5,865,802 A | 2/1999 | Yoon et al. |
| 5,875,782 A | 3/1999 | Ferrari et al. |
| 5,879,291 A | 3/1999 | Kolata et al. |
| 5,893,866 A | 4/1999 | Hermann et al. |
| 5,906,577 A | 5/1999 | Beane et al. |
| 5,908,382 A | 6/1999 | Koros et al. |
| 5,925,058 A | 7/1999 | Smith et al. |
| 5,931,778 A | 8/1999 | Furnish |
| 5,935,107 A | 8/1999 | Taylor et al. |
| 5,944,736 A | 8/1999 | Taylor et al. |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | de la Torre et al. |
| 6,033,362 A | 3/2000 | Cohn |
| 6,033,425 A | 3/2000 | Looney et al. |
| 6,036,641 A | 3/2000 | Taylor et al. |
| 6,048,309 A | 4/2000 | Flom et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 | 7/2001 | Fadem et al. |
| 6,254,534 B1 | 7/2001 | Butler et al. |
| 6,283,912 B1 | 9/2001 | Hu et al. |
| 6,309,349 B1 | 10/2001 | Bertolero et al. |
| 6,312,377 B1 | 11/2001 | Segermark et al. |
| 6,331,158 B1 | 12/2001 | Hu et al. |
| 6,332,468 B1 | 12/2001 | Benetti |
| 6,354,995 B1 | 3/2002 | Hoftman et al. |
| 6,361,492 B1 | 3/2002 | Santilli |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,382,211 B1 | 5/2002 | Crook |
| 6,432,121 B1 | 8/2002 | Jervis |
| 6,443,957 B1 | 9/2002 | Addis |
| 6,447,529 B2 | 9/2002 | Fogarty et al. |
| 6,450,983 B1 | 9/2002 | Rambo |
| 6,458,079 B1 | 10/2002 | Cohn et al. |
| 6,468,205 B1 | 10/2002 | Mollenauer et al. |
| 6,500,116 B1 | 12/2002 | Knapp |
| 6,506,200 B1 | 1/2003 | Chin |
| 6,514,272 B1 | 2/2003 | Kieturakis et al. |
| 6,517,514 B1 | 2/2003 | Campbell |
| 6,517,563 B1 | 2/2003 | Paolitto et al. |
| 6,527,787 B1 | 3/2003 | Fogarty et al. |
| 6,540,764 B1 | 4/2003 | Kieturakis et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Segermark et al. |
| 6,746,467 B1 | 6/2004 | Taylor et al. |
| 6,796,960 B2 | 9/2004 | Cioanta et al. |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,300,448 B2 | 11/2007 | Criscuolo et al. |
| 7,314,364 B2 | 1/2008 | Mahoney et al. |
| 7,344,495 B2 | 3/2008 | Ravikumar et al. |
| 7,387,126 B2 | 6/2008 | Cox et al. |
| 7,393,322 B2 | 7/2008 | Wenchell |
| 7,473,222 B2 | 1/2009 | Dewey et al. |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |
| 7,594,888 B2 | 9/2009 | Raymond et al. |
| 7,650,887 B2 | 1/2010 | Nguyen et al. |
| 7,691,089 B2 | 4/2010 | Gresham |
| 8,454,645 B2 | 6/2013 | Criscuolo et al. |
| 8,926,508 B2 | 1/2015 | Hotter |
| 10,022,149 B2 | 7/2018 | Holsten et al. |
| 2001/0002429 A1 | 5/2001 | Hu et al. |
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0191371 A1 | 10/2003 | Smith et al. |
| 2004/0049099 A1 | 3/2004 | Ewers et al. |
| 2004/0054353 A1 | 3/2004 | Taylor |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1 | 1/2006 | Douglas |
| 2006/0089537 A1 | 4/2006 | Schoellhorn |
| 2006/0106416 A1 | 5/2006 | Raymond et al. |
| 2006/0129165 A1 | 6/2006 | Edoga et al. |

(56) References Cited

U.S. PATENT DOCUMENTS

| | | |
|---|---|---|
| 2006/0149137 A1 | 7/2006 | Pingleton et al. |
| 2006/0149306 A1 | 7/2006 | Hart et al. |
| 2006/0155170 A1 | 7/2006 | Hanson et al. |
| 2007/0010846 A1 | 1/2007 | Leung et al. |
| 2007/0027364 A1 | 2/2007 | Schwer |
| 2007/0073110 A1 | 3/2007 | Larson et al. |
| 2007/0239108 A1* | 10/2007 | Albrecht ............... A61M 39/06 604/167.03 |
| 2008/0132766 A1 | 6/2008 | Dant et al. |
| 2008/0234550 A1 | 9/2008 | Hawkes et al. |
| 2009/0204067 A1 | 8/2009 | Abu-Halawa |
| 2009/0265941 A1 | 10/2009 | Kurrus |
| 2009/0299148 A1 | 12/2009 | White et al. |
| 2010/0210916 A1 | 8/2010 | Hu et al. |
| 2010/0234689 A1 | 9/2010 | Wagner et al. |
| 2020/0100814 A1 | 4/2020 | Zhu |
| 2020/0155815 A1 | 5/2020 | Giasolli et al. |
| 2021/0093842 A1 | 4/2021 | Daly |

FOREIGN PATENT DOCUMENTS

| | | |
|---|---|---|
| EP | 0177177 A2 | 4/1986 |
| EP | 0480653 A1 | 4/1992 |
| EP | 0610099 A2 | 8/1994 |
| EP | 0880939 A1 | 12/1998 |
| EP | 2179699 A1 | 4/2010 |
| EP | 2228014 A1 | 9/2010 |
| EP | 2228024 A1 | 9/2010 |
| EP | 2238931 A1 | 10/2010 |
| EP | 2417922 A1 | 2/2012 |
| EP | 2959865 A1 | 12/2015 |
| EP | 3115077 A1 | 1/2017 |
| GB | 2275420 A | 8/1994 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9500197 A1 | 1/1995 |
| WO | 9515715 A1 | 6/1995 |
| WO | 9721461 A1 | 6/1997 |
| WO | 9912602 A1 | 3/1999 |
| WO | 0108563 A2 | 2/2001 |
| WO | 0126724 A2 | 4/2001 |
| WO | 02096307 A2 | 12/2002 |
| WO | 03034908 A2 | 5/2003 |
| WO | 2004032756 A2 | 4/2004 |
| WO | 2005089655 A1 | 9/2005 |
| WO | 2010136805 A1 | 12/2010 |
| WO | 2011079374 A1 | 7/2011 |
| WO | 2013134696 A1 | 9/2013 |
| WO | 2016186905 A1 | 11/2016 |

\* cited by examiner

SURGICAL ACCESS DEVICE HAVING A BALLOON AND METHODS FOR MANUFACTURING THE SAME

The present disclosure relates generally to surgical access devices. In particular, the present disclosure relates to a surgical access device having a balloon and methods for manufacturing the same.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor to prevent the cannula from backing out of the opening in the abdominal wall, for example, during withdrawal of the laparoscopic instrument from the cannula.

SUMMARY

This disclosure generally relates to methods for manufacturing a balloon for a surgical access device. The methods form a balloon having a plurality of protrusions extending radially outwardly from an inflatable anchor of the balloon. The protrusions may enhance the function and/or performance of the balloon by, for example, strengthening the inflatable anchor and/or increasing fixation force within tissue.

In one aspect, the disclosure provides a method of forming a balloon for a surgical access device including positioning a molding material into a channel defined in a first mold half of a mold and mounting a second mold half onto the first mold half to cover the channel and form a cavity within the mold. The first and second mold halves each includes vent holes extending therethrough that are in fluid communication with the cavity. The method also includes expanding the molding material to conform to the shape of the cavity to form a balloon including protrusions extending radially outwardly therefrom. The protrusions are formed by engagement of the molding material with the vent holes.

In aspects, the cavity of the mold may include an intermediate portion having a toroidal shape, and expanding the molding material may include forming an inflatable anchor of the balloon. The cavity of the mold may include first and third portions disposed on opposed sides of the intermediate portion with each having a tubular shape. Expanding the molding material may include forming proximal and distal sleeves of the balloon.

In another aspect, expanding the molding material may include subjecting the molding material to gas, pressure, or increased temperature. The molding material may be a tube, and expanding the molding material may include blow molding the tube.

In a further aspect, the method may include curing the expanded molding material and/or removing the balloon from the mold.

In another aspect, the disclosure provides a surgical access device including a cannula including an elongated shaft having a distal end portion operably coupled to a balloon. The elongated shaft includes an inflation lumen extending therethrough in communication with an interior of the balloon such that the balloon is transitionable between a collapsed position and an expanded position. The balloon includes protrusions extending radially outwardly therefrom.

In an aspect, the interior of the balloon may be defined within an inflatable anchor of the balloon, and the protrusions may be formed in the inflatable anchor. The inflatable anchor and the protrusions may be integrally formed from a common material. The inflatable anchor may have a generally toroidal shape. The balloon may include a proximal sleeve extending proximally from the inflatable anchor and a distal sleeve extending distally from the inflatable anchor, the proximal and distal sleeves hermetically sealed to the elongated shaft.

In aspects, the protrusions may be disposed circumferentially around the balloon in spaced relation relative to each other. The protrusions may be formed in a central portion of the balloon. The protrusions may extend from an apex of the balloon when in the expanded position. The protrusions may each have a circular shape.

In another aspect, the elongated shaft may have a proximal end portion operably coupled to an anchor inflation port, and the inflation lumen of the elongated shaft may be in fluid communication with the anchor inflation port. An instrument housing may be coupled to the proximal end portion of the cannula and may be disposed proximally of the anchor inflation port.

The details of one or more aspects of the disclosure are set forth in the accompanying drawings and the description below. Other features, objects, and advantages of the aspects described in this disclosure will be apparent from the description and drawings, and from the claims.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
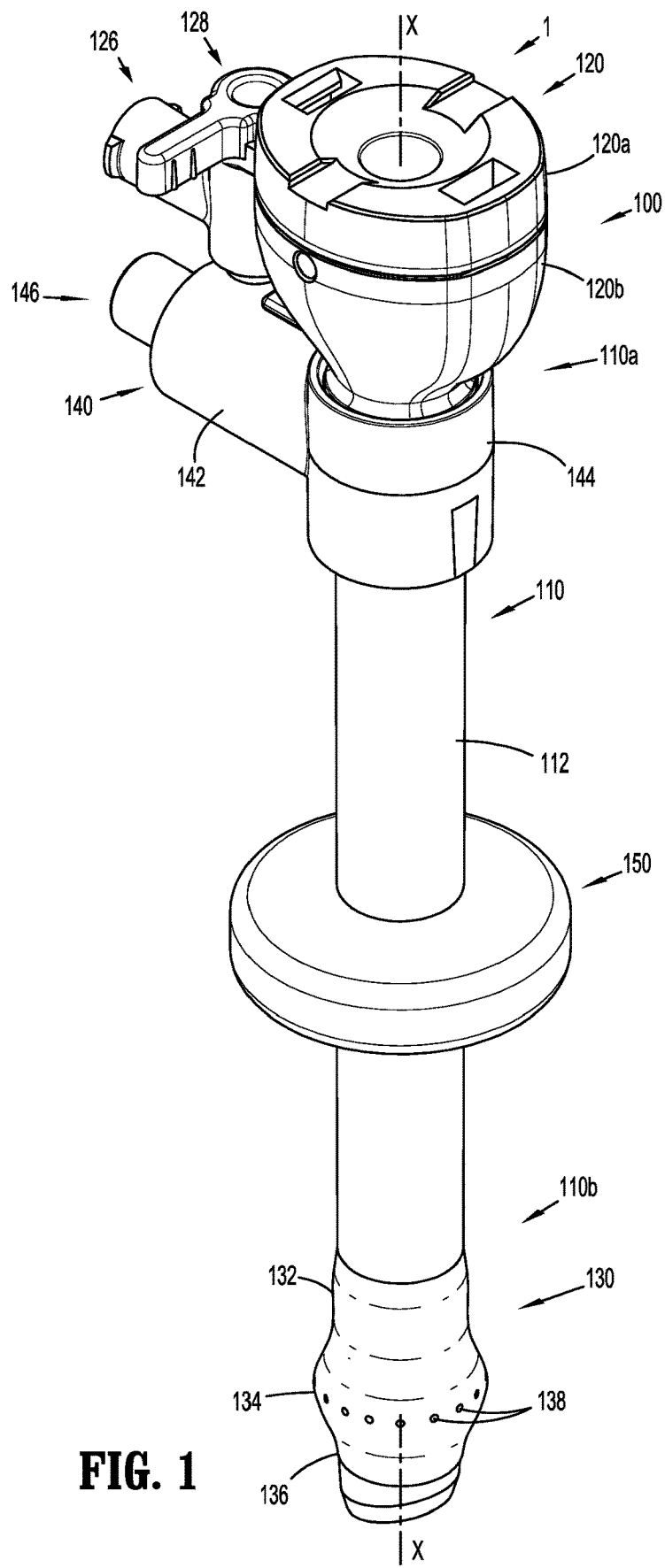
FIG. 1 is a perspective view of a surgical access assembly in accordance with an aspect of the disclosure, shown with a balloon in a collapsed position.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user. The terms "generally," "substantially," and "about" shall be understood as words of approximation that take into account relatively little to no variation in the modified terms (e.g., differing by less than 10%).

Figure 2:
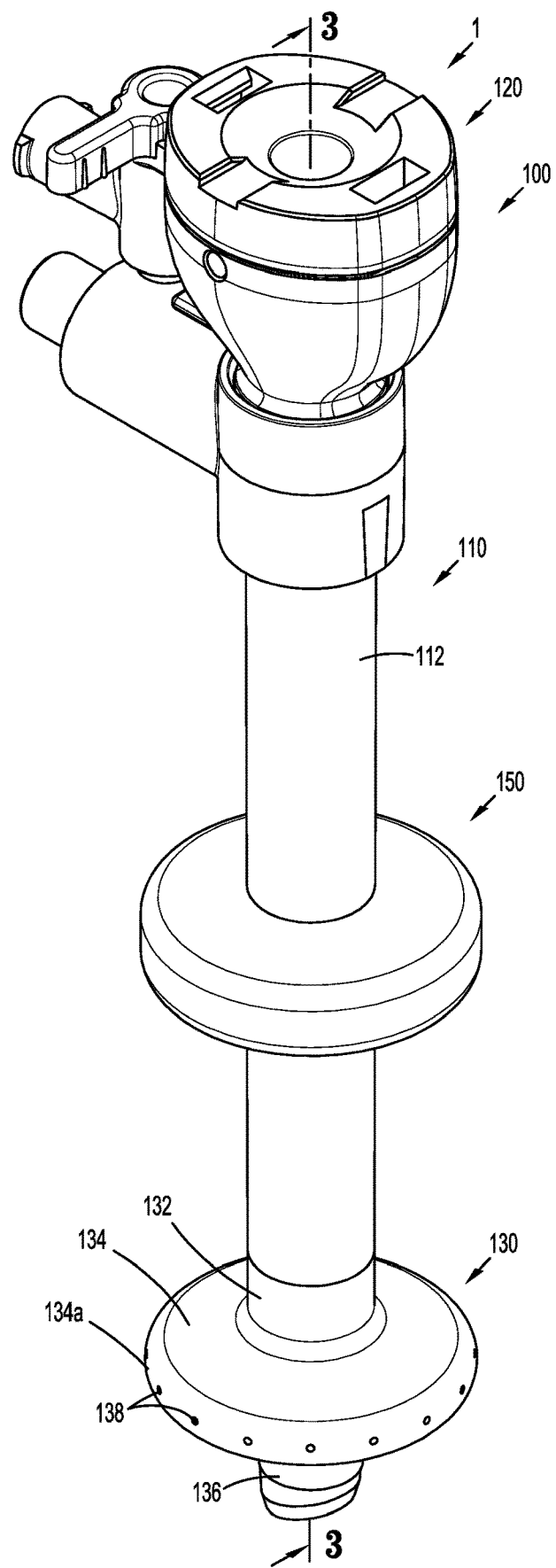
FIG. 2 is a perspective view of the surgical access assembly of FIG. 1, shown with the balloon in an expanded position.
Figure 3:
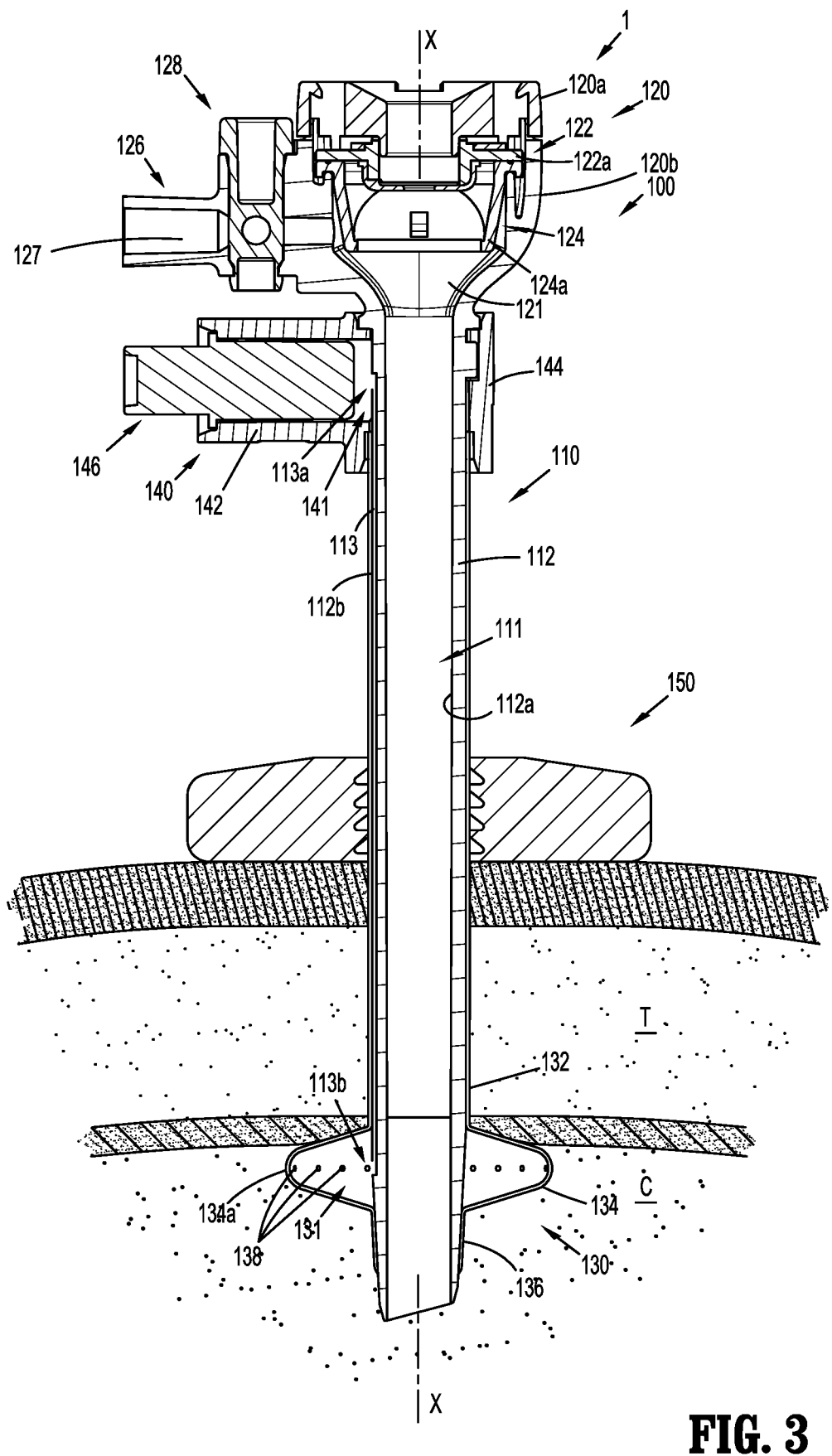
FIG. 3 is a cross-sectional view of the surgical access assembly of FIG. 2, taken along section line 3-3 of FIG. 2, shown secured to tissue.

FIGS. 1-3 illustrates a surgical access assembly 1 including a surgical access device 100 including a balloon 130 formed in accordance with aspects of the present disclosure and a retention collar 150 supported on the surgical access device 100. The surgical access assembly 1 will further be described to the extent necessary to disclose aspects of the disclosure. For a detailed description of the structure and function of components of exemplary surgical access assemblies, surgical access devices, and/or retention collars, reference may be made to U.S. Pat. Nos. 7,300,448; 7,691,089; and 8,926,508, the entire content of each of which is hereby incorporated by reference herein. Accordingly, it should be understood that a variety of surgical access devices and assemblies may utilize a balloon manufactured in accordance with the present disclosure.

The surgical access device 100 includes a cannula 110 and an instrument housing 120 secured to the cannula 110. The cannula 110 generally includes an elongated shaft 112 extending along a longitudinal axis "X." A proximal end portion 110a of the cannula 110 supports the instrument housing 120 thereon and a distal end portion 110b of the cannula 110 supports the balloon 130. The elongated shaft 112 includes an access lumen 111 (FIG. 3) defined by an inner surface 112a of the elongated shaft 112 that extends along the longitudinal axis "X" for reception and passage of a surgical instrument (not shown) therethrough.

As specifically shown in FIG. 3, the elongated shaft 112 also includes an inflation lumen 113 defined between the inner and outer surfaces 112a, 112b of the elongated shaft 112 that extends substantially parallel to the access lumen 112. The inflation lumen 113 is open at a distal end 113b thereof through the outer surface 112b of the elongated shaft 112 such that the inflation lumen 113 is in fluid communication with an interior 131 of the balloon 130. The balloon 130 is transitionable from a collapsed or deflated position, as seen in FIG. 1, in which the balloon 130 is positioned adjacent to or directly against the outer surface 112b of the elongated shaft 112 and an expanded or inflated position, as seen in FIG. 2, in which the balloon 130 extends radially outwardly from the elongated shaft 112. The balloon 130 is movable through an opening in body tissue when in the collapsed position and secures the cannula 110 against an inner surface of a body wall, such as an abdominal wall, when in the expanded position, as seen in FIG. 3.

The balloon 130 includes a proximal sleeve or neck 132, an inflatable or expandable anchor 134 extending distally from the proximal sleeve 132, and a distal sleeve or tail 136 extending distally from the inflatable anchor 134 such that the inflatable anchor 134 is disposed between the proximal and distal sleeves 132, 136. The balloon 130 is positioned around the elongated shaft 112 with the proximal sleeve 132 of the balloon 130 secured to the elongated shaft 112 at a location proximal to the distal end 113b of the inflation lumen 113 and the distal sleeve 136 of the balloon 130 secured to the elongated shaft 112 at a location distal to the distal end 113b of the inflation lumen 113. The proximal and distal sleeves 132, 136 of the balloon 130 are secured to the elongated shaft 112 (e.g., by adhesives and/or welding) to create hermetic contact therebetween. The inflatable anchor 134 is positioned over or proximate to the distal end 113b of the inflation lumen 113 such that the interior 131 of the balloon 130 in fluid communication with the inflation lumen 113.

As seen in FIGS. 2 and 3, the inflatable anchor 134 of the balloon 130 has a generally toroidal or ring shape when in the expanded position. A central portion or apex 134a of the inflatable anchor 134 includes protrusions or bumps 138 formed therein and extending radially outwardly therefrom. The apex 134a is a lateral peak when the inflatable anchor 134 is in the expanded position. The protrusions 138 are disposed circumferentially around the inflatable anchor 134 in spaced relation relative to each other. It should be understood that the number of protrusions 138 may vary. For example, while a number of protrusions 138 are shown in FIGS. 2 and 3, the inflatable anchor 134 may include as few as four protrusions 138 disposed at about 90° angles with respect to each other. While the protrusions 138 are shown as having a generally circular shape, it should be understood that other shapes and sizes of the protrusions 138 are envisioned. Further, while the protrusions 138 are shown disposed radially around the inflatable anchor 134, it should be understood that the protrusions 138 may be distributed around the inflatable anchor 134 in other patterns (e.g., evenly distributed across the entirety of the inflatable anchor 134, distributed in laterally spaced bands radially around the inflatable anchor 134, etc.) depending upon the desired characteristics of the inflatable anchor 134. The protrusions 138 may enhance the function and/or performance of the inflatable anchor 134 by, for example, reinforcing and strengthening the inflatable anchor 134 to withstand penetration and/or inflation forces, and/or increasing adherence or grip of the inflatable anchor 134 on tissue to increase the fixation force within the tissue in which the inflatable anchor 134 is positioned.

The retention collar 150 is supported on the elongated shaft 112 of the cannula 110. The retention collar 150 is releasably engageable with the elongated shaft 112, and slidable therealong to adjust the longitudinal position of the retention collar 150 on the elongated shaft 112. The retention collar 150 secures the cannula 110 against an outer surface of a body wall (see e.g., FIG. 3). The retention collar 150 may be formed from a compressible material (e.g., foam, cotton or other suitable textile) or an elastomeric material (e.g., rubber or silicone) to aid in sealing the opening into the tissue of the body wall. The retention collar 150 may be any known retention mechanism used on cannulas and/or trocars, such as foam or rubber collars.

The instrument housing 120 includes an upper housing section 120a and a lower housing section 120b, and defines a cavity 121 (FIG. 3) therein that communicates with the access lumen 111 of the elongated shaft 112 of the cannula 110. The upper housing section 120a may be selectively attachable to, and detachable from, the lower housing section 120b, and the lower housing section 120b may be releasably or permanently attached to the cannula 110. In aspects, either or both of the upper and lower housing sections 120a, 120b of the instrument housing 120 may include knurls, indentations, tabs, or be otherwise configured to facilitate engagement by a user.

As seen in FIG. 3, the instrument housing 120 supports a seal assembly 122 and a valve assembly 124 therein. The seal assembly 122 is disposed proximally of the valve assembly 124. The seal assembly 122 generally includes an instrument seal 122a for sealing around surgical instruments (not shown) inserted into the cannula 110, and the valve assembly 124 generally includes a zero-closure seal 124a for sealing the access lumen 111 of the cannula 110 in the absence of a surgical instrument inserted through the cannula 110. The seal assembly 122 and the valve assembly 124 prevent the escape of the insufflation fluid therefrom, while allowing surgical instruments to be inserted therethrough and into the body cavity. The instrument seal 122a may include any known instrument seal used in cannulas and/or trocars, such as a septum seal. The zero-closure seal 124a may be any known zero-closure seal for closing off the passageway into the access lumen 111, such as a duckbill seal or flapper valve.

The instrument housing 120 includes an insufflation port 126 coupled to the lower housing section 120b. The insufflation port 126 defines an opening 127 therethrough that is in fluid communication with the cavity 121 of the instrument housing 120 which, in turn, is in fluid communication with the access lumen 111 of the cannula 110 to insufflate a body cavity, such as an abdominal cavity (e.g., create a pneumoperitoneum). The opening 127 of the insufflation port 126 is disposed distally of the valve assembly 124 to maintain insufflation pressure within the body cavity. The insufflation port 126 is connectable to a source of insufflation fluid (not shown) for delivery of the insufflation fluid (e.g., gases) into the body cavity. The insufflation port 126 is configured and dimensioned to receive a valve 128 in a substantially fluid-tight manner. In aspects, and as shown, the valve 128 is a stopcock valve for controlling the flow of the insufflation fluid. The valve 128, however, may be any known valve for directing fluid flow and, in some aspects, regulating fluid flow.

The cannula 110 includes an anchor inflation port 140 coupled to the elongated shaft 112. The anchor inflation port 140 includes a housing 142 and a collar 144 extending from the housing 142. The collar 144 secures the housing 142 to the elongated shaft 112. The collar 144 extends around the elongated shaft 112 and is engaged with the elongated shaft 112 in a manner that fixes (e.g., longitudinally and rotationally) the anchor inflation port 140 relative to the elongated shaft 112. More particularly, the collar 144 is engaged with the elongated shaft 112 by snap fit connection, and is further seated thereover in a friction fit manner. It should be understood that other mating structures and relationships may be utilized to secure the anchor inflation port 140 to the elongated shaft 112 (e.g., bayonet coupling, tongue and groove arrangement, threaded arrangement, etc.).

The anchor inflation port 140 is in fluid communication with the balloon 130. The housing 142 of the anchor inflation port 140 defines a cavity 141 therein that is in fluid communication with the inflation lumen 113 of the cannula 110 which, in turn, is in fluid communication with the balloon 130, as described above. A proximal end 113a of the inflation lumen 113 is disposed within the cavity 141 of the housing 142 of the anchor inflation port 140 to provide an inlet from a fluid source (not shown) during inflation and an outlet into the cavity 141 during deflation such that the inflation lumen 113 provides a pathway for fluid flow from the fluid source to the balloon 130. The housing 142 is connectable to the fluid source for delivery of a fluid (e.g., gases) into the balloon 130. The anchor inflation port 140 may include a valve 146 for delivery and removal of fluid into and out of the balloon 130. For example, a syringe (not shown) may be coupled to the valve 146 to deliver air into the balloon 130 or to remove air from the balloon 130. Alternatively, the anchor inflation port 140 may include inlet and outlet valves (e.g., a check valve and a release valve, respectively) operably coupled to the housing 142 in a substantially fluid-tight manner. The anchor inflation port 140 may further include a relief valve (not shown) to limit the pressure that can build up in the balloon 130. It should be understood that any known valves for controlling fluid flow may be coupled to the anchor inflation port 140.

FIG. 3 illustrates the surgical access assembly 1 disposed within tissue "T," e.g., an abdominal wall. The elongated shaft 112 of the cannula 110 is received through the tissue "T" (e.g., by utilizing an obturator (not shown) to facilitate entry of the cannula 110 through the tissue "T"), and the balloon 130 is inflated within a body cavity "C" to prevent the cannula 110 from being withdrawn through the tissue "T." The retention collar 150 is slid distally along the elongated shaft 112 of the cannula 110 until the retention collar 150 abuts or presses on the tissue "T." The tissue "T" is thus sandwiched between the balloon 130 and the retention collar 150 to prevent the cannula 110 from being withdrawn from or over-inserted into the tissue "T." In this manner, the surgical access assembly 1 is secured to the tissue "T" and longitudinal movement of the cannula 110 relative to the tissue "T" is prevented or minimized throughout insertion, withdrawal, and/or manipulation of a surgical instrument (not shown) through the cannula 110. Following the surgical procedure, the balloon 130 is deflated to permit the withdrawal of the surgical access assembly 1 from the tissue "T."

Figure 4:
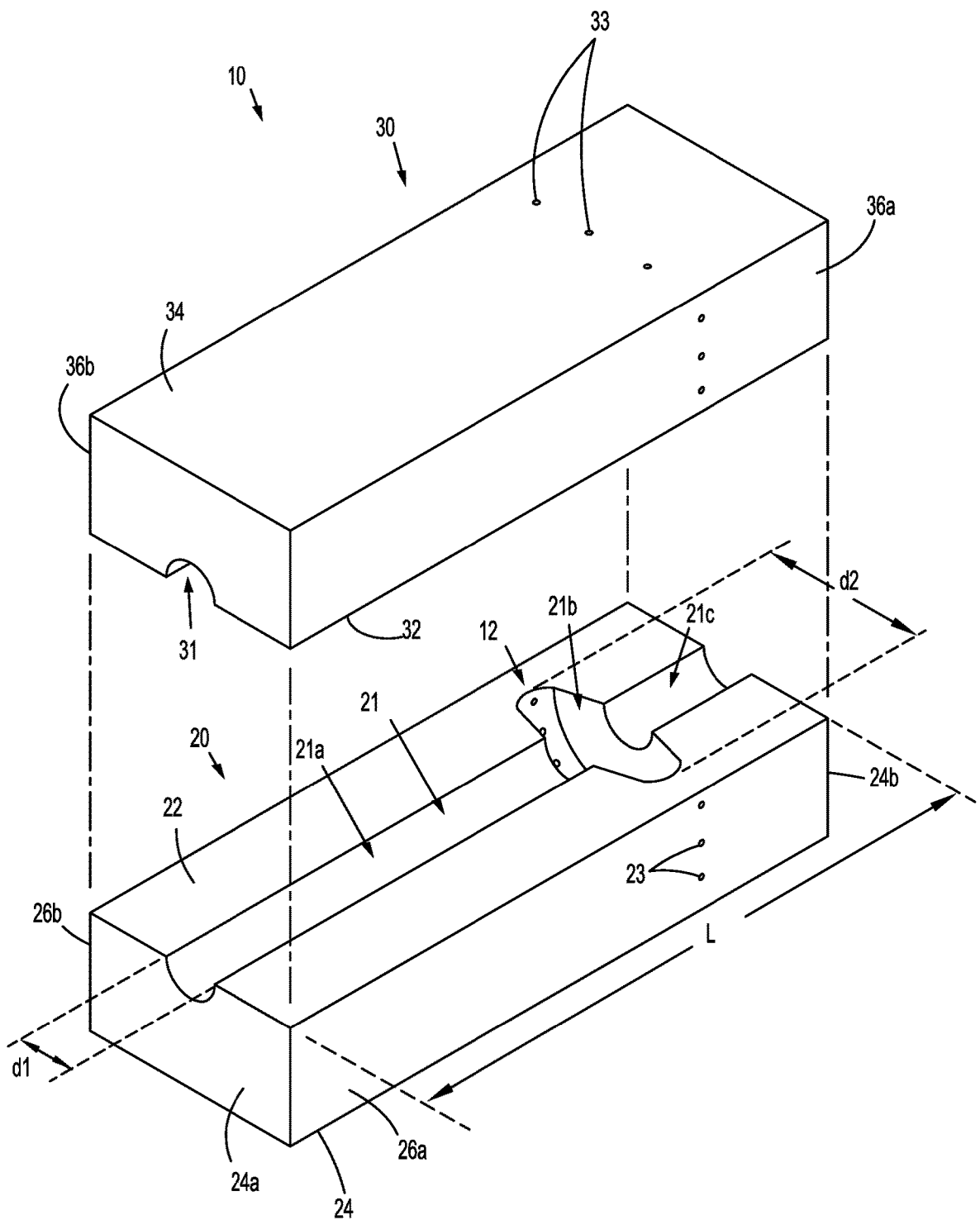
FIG. 4 is a perspective view of a mold for forming the balloon of FIG. 1, shown with first and second mold halves separated.

Turning now to FIGS. 4-8, a mold 10 for forming the balloon 130 in accordance with aspects of the present disclosure is shown. The mold 10 includes first and second mold halves or portions 20, 30. The first and second mold halves 20, 30 each include an inner surface 22, 32 defining a channel 21, 31 therein, which together form a cavity 11 for holding a molding material 40. The cavity 11 defines a geometry capable of forming the balloon 130. While only the inner surface 22 and the channel 21 of the first mold half 20 is shown in FIG. 4, it should be understood that the inner surface 32 and the channel 31 of the second mold half 30 is substantially identical to that of the first mold half 20 and is a mirror image of the first mold half 20 as seen, for example, in FIG. 6. Accordingly, when the inner surfaces 22, 32 of the first and second mold halves 20, 30 mate, the inner surface 32 of the second mold half 30 directly abuts the inner surface 22 of the first mold half 20 and the channels 21, 31 align to form the cavity 11 within the mold 10. It should be further understood that while the first and second mold halves 20, 30 are substantially symmetrical, the first and second mold halves 20, 30 may be different.

The channel 21 of the first mold half 20 extends the length "L" of the first mold half 20 and is open at end surfaces 24a, 24b of the first mold half 20. The channel 21 has a first portion 21a, a second or intermediate portion 21b, and a third portion 21c that forms one half of a first portion 11a, a second or intermediate portion 11b, and a third portion 11c of the cavity 11 when the first mold half 20 is mated with the second mold half 30. The first portion 11a of the cavity 11 corresponds to the desired length and form of the proximal sleeve 132 of the balloon 130, the second portion 11b corresponds to the desired length and form of the inflatable anchor 134 of the balloon 130, and the third portion 11c corresponds to the desired length and form of the distal sleeve 136 of the balloon 130.

The first and third portions 21a, 21c of the channel 21 have a substantially semicircular shape such that when the channels 21, 31 of the first and second mold halves 20, 30 are mated, the first and third portions 11a, 11c of the cavity 11 have a tubular configuration having an inner diameter "d1" that is constant along the length thereof. The inner diameter "d1" of the first and third portions 11a, 11c are substantially the same as each other and are sized so that the proximal and distal sleeves 132, 136 (FIG. 8) of a balloon 130 formed therein are engageable with an elongated shaft of a surgical access device. The second portion 21b of the channel 21 has a substantially semi-annular shape such that when the channels 21, 31 of the second mold halves 20, 30 are mated, the second portion 11b of the cavity 11 has a toroidal or ring-shaped configuration having an inner diameter "d2" that varies along the length thereof. The inner diameter "d2" is largest at an apex 12 of the second portion 11b of the cavity 11 that correspond with the apex 134a of the inflatable anchor 134 and tapers towards the first and third portions 11a, 11c such that the inner diameter "d2" of the second portion 11b is larger than the inner diameter "d1" of the first and third portions 11a, 11c. The second portion 11b is sized, such that in the expanded position, the inflatable anchor 134 of the balloon 130 formed therein extends radially outwardly from the proximal and distal sleeves 132, 136 to engage tissue.

The first and second mold halves 20, 30 further includes pores or vent holes 23, 33. The vent holes 23 of the first mold half 20 extend through the inner surface 22 to an outer surface 24 or side surfaces 26a, 26b of the first mold half 20 such that each vent hole 23 is in fluid communication with the channel 21 of the first mold half 20 and the outside environment. Likewise, the vent holes 33 of the second mold half 30 extend through the inner surface 32 to an outer surface 34 or side surfaces 36a, 36b of the second mold half 30 such that each vent hole 33 is in fluid communication with the channel 31 of the second mold half 30 and the outside environment. The vent holes 23, 33 are open at the apex 12 of the second portion 11b of the cavity 11 and extend radially outwardly therefrom and circumferentially therearound in spaced relation relative to each other. The vent holes 23, 33 allow the molding material 40 to vent within the cavity 11 and aid in shaping the protrusions 138 on the balloon 130. The vent holes 23, 33 have a substantially circular shape that are about 1 mm or less in size. It should be understood that other positions, shapes, and/or sizes of the vent holes 23, 33 are envisioned.

Figure 5:
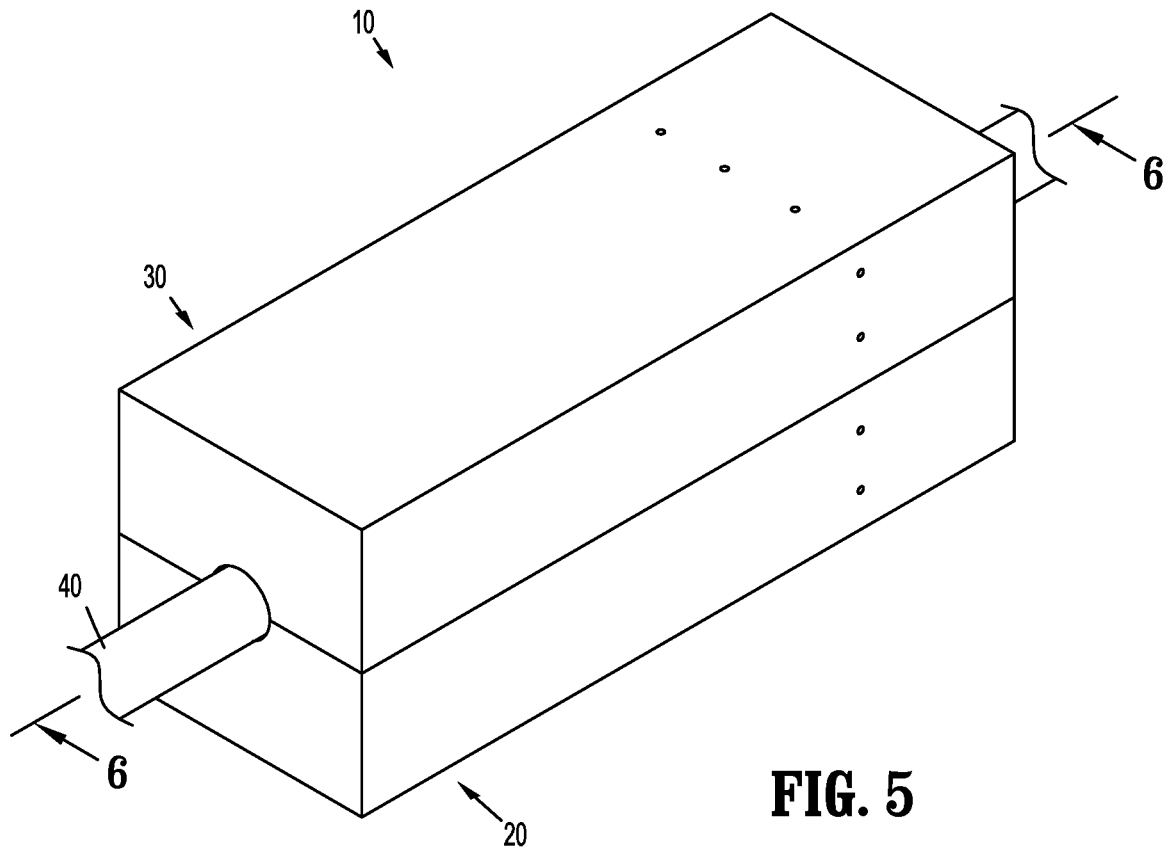
FIG. 5 is a perspective view of the mold of FIG. 4, shown with the first and second mold halves mated and a molding material positioned therein.
Figure 6:
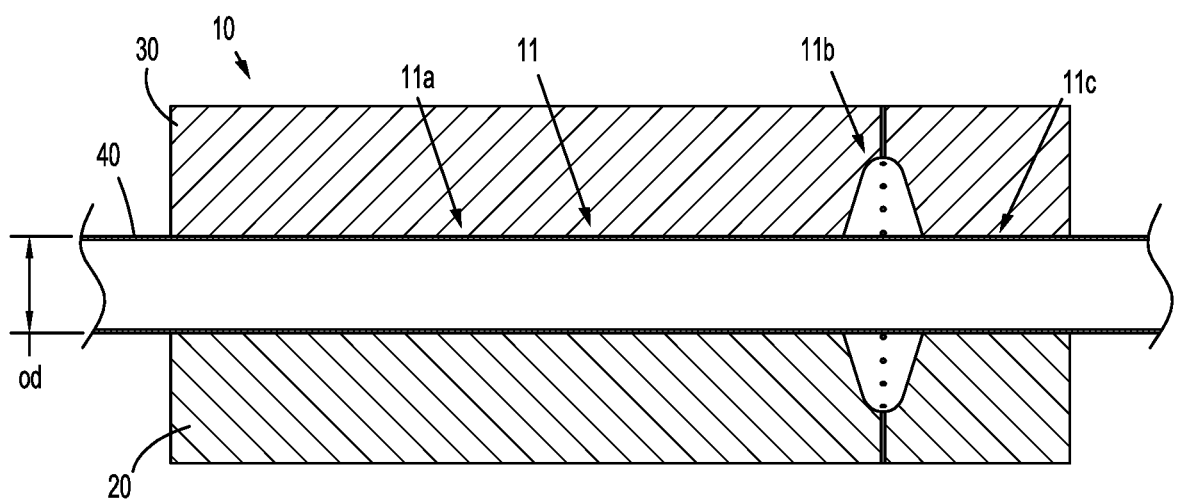
FIG. 6 is a cross-sectional view of the mold of FIG. 5, taken along section line 6-6 of FIG. 5, shown with the molding material in an unexpanded state.

In a method of forming a balloon 130, a length of mold material 40 formed, for example, from an elastic material, is placed within the channel 21 of the first mold half 20 such that the molding material 40 extends across the entire length "L" of the first mold half 20 and beyond the end surfaces 24a, 24b, as seen in FIGS. 4 and 5. The mold material 40 may be balloon tubing (e.g., a tube formed by extruding a polymeric material). The second mold half 30 is placed over the first mold half 20 such that the inner surfaces 22, 32 of the first and second mold halves 20, 30 abut each other and the channels 21, 31 align to form the cavity 11 of the mold 11, retaining the molding material 40 therein, as seen in FIGS. 5 and 6. Portions of the molding material 40 extending outside of the mold 40 may be held to apply axial tension on the molding material 40. After the first and second mold halves 20, 30 are mated, the first and second mold halves 20, 30 may be releasably secured together using, for example, clamps, bands, tape, etc.

Figure 7:
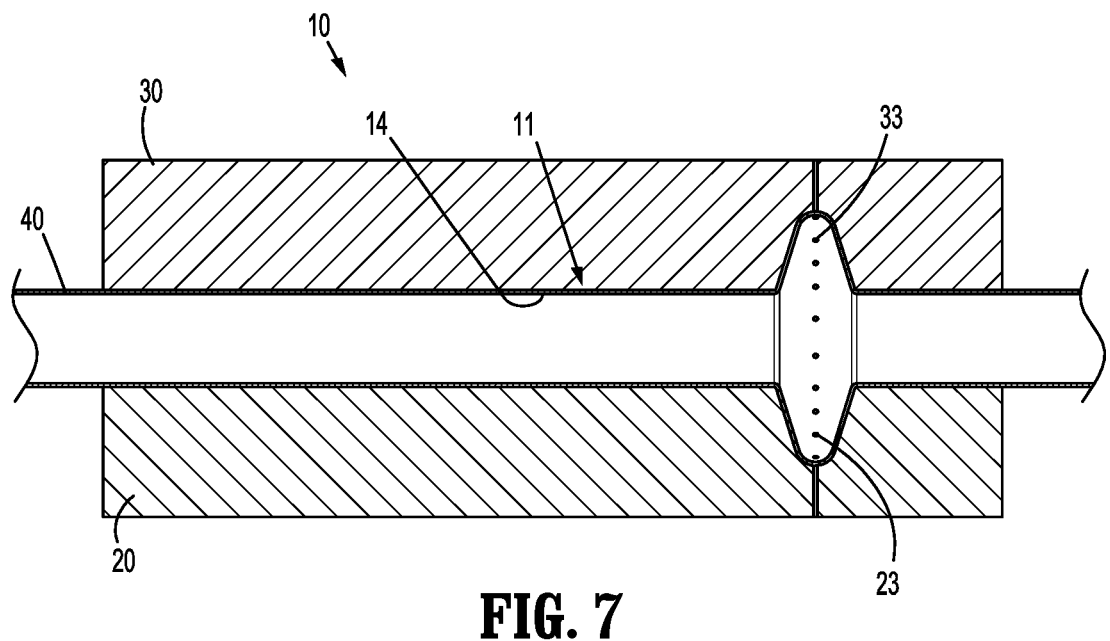
FIG. 7 is a cross-sectional view of the mold of FIG. 6, shown with the molding material in an expanded state.

The molding material 40 is then expanded within the mold 10 into contact with an interior surface 14 of the cavity 11 and partially into the vent holes 23, 33 of the mold 10 by the application of gas (e.g., air), pressure, and/or heat, as seen in FIG. 7. The molding material 40 may be expanded into the shape of the balloon 130 by blow molding, in which gas is passed into the molding material 40 (which is preformed into a tube, as discussed above, prior to placement within the mold 10) and the pressure from the gas expands the molding material 40 to match the shape of the cavity 11. While the molding material 40 is shown as having an unexpanded outer diameter "od" that is substantially the same as the inner diameter "d1" of the first and third portions 11a, 11c of the cavity 11 such that little to no radial expansion of the molding material 40 occurs in the first and third portion 11a, 11c of the cavity 11, it should be understood that alternatively, the molding material 40 may have an unexpanded outer diameter "od" that is smaller than the inner diameter "d1" of the first and third portions 11a, 11b such that the molding material 40 is expanded within the first and third portions 11a, 11c.

Figure 8:
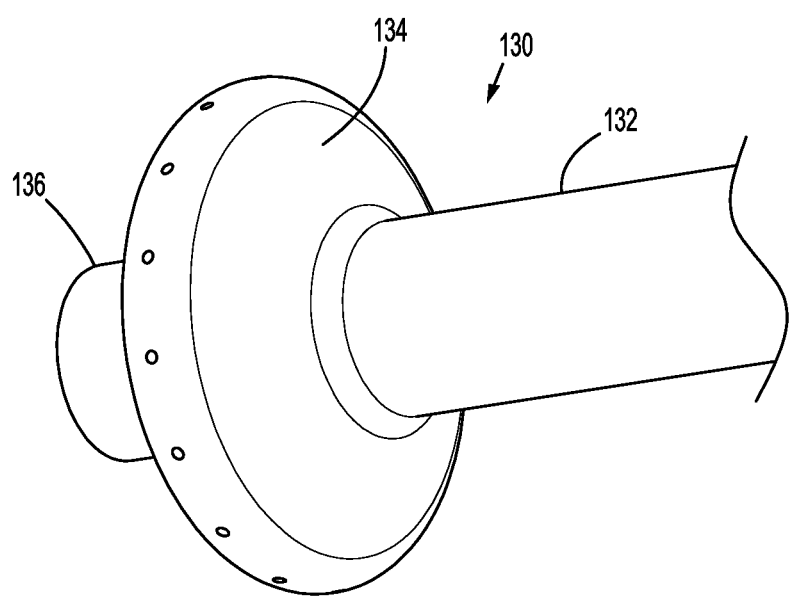
FIG. 8 is a perspective view of a balloon formed from the expanded molding material of FIG. 7.

The expanded molding material 40 remains in the mold 10 until it has solidified and cured. Thereafter, the mold 10 is opened and the now formed balloon 130, as shown in FIG. 8, is removed therefrom. It should be understood that the expanded molding material 40 may be further treated, e.g., annealed or heat treated, within the mold 10 or after removal therefrom, and may be trimmed prior to bonding to the elongated shaft 112. The protrusions 138 on the formed balloon 130 may also be inspected and used as visual indicators that the balloon 130 is fully formed and of correct dimension and design. The balloon 130 may then be secured to the elongated shaft 112, as described above, such that application of fluid from the fluid source expands the inflatable anchor 134 of the balloon 130.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical access device comprising:
a cannula including an elongated shaft having a distal end portion operably coupled to a balloon, the elongated shaft including an inflation lumen extending through the elongated shaft in communication with an interior of the balloon such that the balloon is transitionable between a collapsed position and an expanded position,
wherein in the expanded position, the balloon includes a single row of protrusions extending radially outwardly from an outside surface of the balloon, the outside surface of the balloon tapering on either side of a central plane to a lateral apex, the single row of protrusions extending from the lateral apex.

2. The surgical access device according to claim 1, wherein the interior of the balloon is defined within an inflatable anchor of the balloon, and the single row of protrusions is formed in the inflatable anchor.

3. The surgical access device according to claim 2, wherein the inflatable anchor and the single row of protrusions are integrally formed from a common material.

4. The surgical access device according to claim 2, wherein the inflatable anchor has a generally toroidal shape.

5. The surgical access device according to claim 2, wherein the balloon includes a proximal sleeve extending proximally from the inflatable anchor and a distal sleeve extending distally from the inflatable anchor, the proximal and distal sleeves hermetically sealed to the elongated shaft.

6. The surgical access device according to claim 1, wherein the single row of protrusions is disposed circumferentially around the balloon, and wherein each protrusion of the single row of protrusions is in spaced relation relative to other protrusions of the single row of protrusions.

7. The surgical access device according to claim 1, wherein the single row of protrusions is formed in a central portion of the balloon.

8. The surgical access device according to claim 1, wherein each protrusion of the single row of protrusions has a circular shape.

9. The surgical access device according to claim 1, wherein the elongated shaft has a proximal end portion operably coupled to an anchor inflation port, and the inflation lumen of the elongated shaft is in fluid communication with the anchor inflation port.

10. The surgical access device according to claim 9, further comprising an instrument housing coupled to the proximal end portion of the cannula, the instrument housing disposed proximally of the anchor inflation port.

* * * * *